(12) United States Patent
Williams et al.

(10) Patent No.: US 9,427,575 B2
(45) Date of Patent: Aug. 30, 2016

(54) EXTENDABLE IMPLANTABLE ELONGATED MEMBER

(75) Inventors: Terrell M. Williams, Brooklyn Park, MN (US); Mark T. Marshall, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 1766 days.

(21) Appl. No.: 12/423,428

(22) Filed: Apr. 14, 2009

(65) Prior Publication Data

US 2009/0259282 A1 Oct. 15, 2009

Related U.S. Application Data

(60) Provisional application No. 61/045,159, filed on Apr. 15, 2008.

(51) Int. Cl.
*A61N 1/00* (2006.01)
*A61N 1/05* (2006.01)

(52) U.S. Cl.
CPC ............. *A61N 1/0587* (2013.01); *A61N 1/056* (2013.01)

(58) Field of Classification Search
CPC ............................ A61N 1/056; A61N 1/0587
USPC ......................................... 607/119, 122, 137
See application file for complete search history.

(56) References Cited

U.S. PATENT DOCUMENTS

| | | | |
|---|---|---|---|
| 3,598,128 A | 8/1971 | Chardack | |
| 3,913,587 A * | 10/1975 | Newash | ............................ 604/8 |
| 4,013,081 A | 3/1977 | Kolenik | |
| 5,324,321 A | 6/1994 | Pohndorf et al. | |
| 5,514,176 A * | 5/1996 | Bosley, Jr. | .................... 623/1.15 |
| 5,897,585 A * | 4/1999 | Williams | ....................... 607/122 |
| 6,178,355 B1 | 1/2001 | Williams et al. | |
| 6,516,230 B2 | 2/2003 | Williams et al. | |
| 6,671,553 B1 | 12/2003 | Helland et al. | |
| 7,184,838 B2 | 2/2007 | Cross, Jr. | |
| 7,238,883 B2 | 7/2007 | Zarembo | |
| 2004/0054390 A1 | 3/2004 | Zarembo et al. | |
| 2007/0016276 A1* | 1/2007 | Heil et al. | ..................... 607/119 |
| 2007/0205014 A1 | 9/2007 | Zarembo | |

FOREIGN PATENT DOCUMENTS

GB 1 570 087 6/1980

OTHER PUBLICATIONS

Shi-Ang Xu, MD. et al., "Evaluation of Expandable Leadwires for Pediatric Cochlear Implants", American Journal of Otology, 14(2); 151-160, Mar. 1993 (Abstract only).
PCT International Search Report, PCT/US2009/040596, 4 pgs.

* cited by examiner

*Primary Examiner* — Niketa Patel
*Assistant Examiner* — Lindsey G Hankins
(74) *Attorney, Agent, or Firm* — Evans M. Mburu; Stephen W. Bauer

(57) ABSTRACT

An extendable medical lead comprises a lead body and a sheath defining a cavity that encloses a length of the lead body. The length of the lead body enclosed within the sheath may be coiled or otherwise gathered such that when extended, the length of the enclosed section of the lead body is greater than the length of the sheath. The sheath may include a seal to help prevent contaminant entry into the cavity in order to help reduce tissue in growth around the length of the lead body disposed within the sheath. A portion of the length of the lead body enclosed within the sheath exits the cavity through an aperture defined by the seal when a tensile force is applied to the lead body.

27 Claims, 7 Drawing Sheets

EXTENDABLE IMPLANTABLE ELONGATED MEMBER

CROSS-REFERENCE TO RELATED APPLICATION

This application claims the benefit of 61/045,159, filed Apr. 15, 2008. The disclosure of the above application is incorporated herein by reference.

TECHNICAL FIELD

The disclosure generally relates to medical devices, and more particularly relates to an extendable medical lead.

BACKGROUND

An implantable medical device, such as a cardiac pacemaker, may deliver therapy (e.g., electrical stimulation or a drug) to a patient via a medical lead. In the case of pacing and/or defibrillation therapy, for example, a distal end of the lead carrying the electrode may be anchored proximate to a heart of a patient, and the proximal end of the lead may be anchored to or proximate to a pacemaker. If the patient is still growing while the medical device is implanted within the patient, such as in the case of a pediatric patient, the distance between the pacemaker and the electrode at the distal end of the lead may generally increase over time. If, however, both the distal and proximal ends of the lead are substantially fixed, the patient's growth may result in tensile forces that pull on either the distal and/or proximal ends of the lead. It is therefore desirable to develop new devices that address tensile forces.

SUMMARY OF THE DISCLOSURE

In general, the disclosure is directed to extendable medical elongated members, such as medical leads or catheter including a fluid delivery conduit, which include a partially coiled or otherwise gathered lead body disposed within a sheath. The elongated member is configured to be coupled to a medical device to deliver a therapy from the medical device to a target therapy delivery site in a patient. The therapy may be electrical stimulation, drug delivery or both.

In an unextended state, the length of the elongated member disposed within the sheath is greater than the length of the sheath. Upon application of a tensile force to the elongated member (e.g., in a direction substantially parallel to a longitudinal axis of the sheath), at least a portion of the length of the elongated member disposed within the sheath exits the sheath, effectively increasing a total length of the elongated member. The elongated member may exit the sheath at either a sheath distal end, sheath proximal end or both. In some embodiments, a seal may be positioned to help prevent contaminant entry into the sheath. Increasing a total length of the elongated member may help decrease any stress applied to an implant site for an implantable medical device and/or stress at the target therapy delivery site due to tensile forces. The tensile forces may be attributable to patient growth or patient movement.

In one embodiment, the disclosure is directed to a medical assembly including an implantable medical elongated member extending between an elongated member proximal end and an elongated member distal end. The medical assembly further includes a sheath defining a cavity. A length of the elongated member is enclosed within the cavity, and the sheath includes a sheath proximal end and a sheath distal end. The medical assembly also includes a seal coupled to at least one of the sheath distal end or the sheath proximal end. The seal defines an aperture through which the elongated member extends, and substantially prevents contaminant entry into the cavity of the sheath. Additionally, a portion of the length of the elongated member enclosed within the sheath exits the cavity through the aperture defined by the seal when a tensile force is applied to the elongated member.

The seal and sheath may be substantially integral, i.e., substantially defines a single unit such that there are no seams between the seal and sheath through which fluid or body tissue may traverse into the cavity defined by the sheath. In some embodiments, a first diameter of the aperture is substantially equal to or less than a second diameter of the elongated member. A section of the length of the elongated member within the cavity may be helically wound in some embodiments, and the helically wound section of the elongated member may be friction fit with the sheath within the cavity.

In another embodiment, the disclosure is directed to an assembly including an elongated member extending between an elongated member distal end and an elongated member proximal end. The assembly also includes a sheath mechanically coupled to the elongated member proximate to the elongated member distal end. The sheath defines a cavity and a first length between a sheath distal end and a sheath proximal end. A second length of the elongated member is enclosed within the cavity, where the second length of the elongated member is greater than the first length of the sheath. The sheath also defines an aperture at the sheath proximal end. A portion of the length of the elongated member enclosed within the sheath exits the cavity through the aperture when a tensile force is applied to the elongated member.

In some embodiments, the assembly further includes a seal mechanically coupled to the sheath proximal end, where the seal defines the aperture and substantially prevents contaminants from entering the cavity of the sheath. Additionally, at least a section of the length of the elongated member within the cavity may be helically wound.

In another embodiment, the disclosure is directed to a method including enclosing a length of a medical elongated member within a sheath including a first length less than a second length of the medical elongated member and sealing a space between the elongated member and sheath to substantially prevent contaminant entry into the sheath. In some embodiments the method includes coiling at least a section of the length of the elongated member.

The details of one or more embodiments are set forth in the accompanying drawings and the description below. Other features, objects, and advantages of the disclosure will be apparent from the description and drawings, and from the claims.

DETAILED DESCRIPTION

Figure 1:
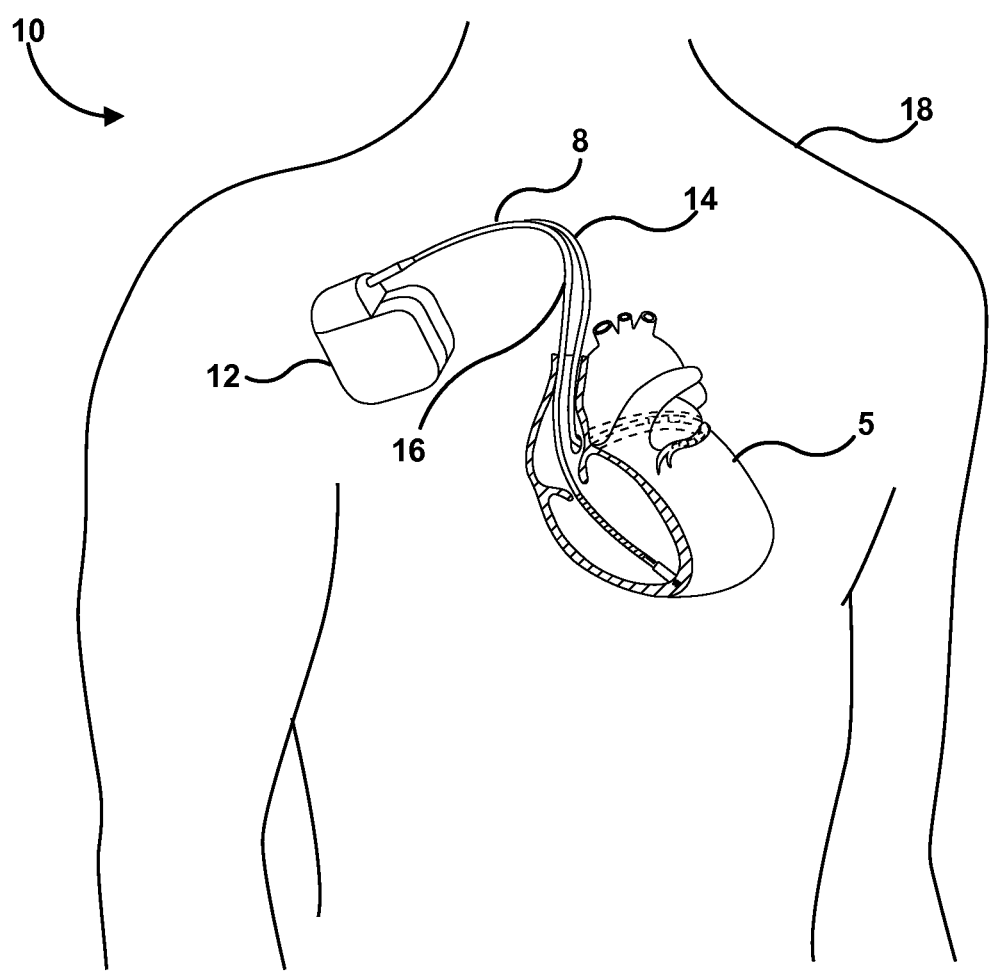
FIG. 1 is a conceptual diagram illustrating an exemplary implantable medical device system.

The present disclosure is generally directed to implantable medical elongated members, such as medical leads or fluid delivery catheters, which include features that facilitate extension of the elongated member as a patient moves or grows. In addition, embodiments are described in which an elongated member includes features that prevent tissue ingrowth around a portion of the elongated member. The elongated member is configured to be coupled to a medical device to deliver a therapy from the medical device to target tissue in a patient. Various embodiments of the elongated member may be applicable to different therapeutic applications. For example, the elongated member may be a stimulation lead or lead extension that is used to deliver electrical stimulation to a target stimulation site and/or sense parameters (e.g., blood pressure, temperature or electrical activity) of a patient. In another embodiment, the elongated member may be a catheter that is placed to deliver a fluid, such as pharmaceutical agents, insulin, pain relieving agents, gene therapy agents, steroids or the like from a fluid delivery device (e.g., a fluid reservoir and/or pump) to a target tissue site in a patient. The disclosure is applicable to any configuration or type of implantable elongated member that is used to deliver therapy to a site in a patient. For purposes of illustration, however, the disclosure will refer to an implantable medical lead including an epicardial electrode for delivery of stimulation to a patient's heart.

While the description primarily refers to implantable medical leads and implantable medical devices, such as pacemakers and defibrillators, that deliver stimulation therapy to a patient's heart, the features of the leads described herein are useful with other types of elongated members, such as fluid delivery catheters, leads including intravenous electrodes, neurostimulation electrodes, and the like, as well as other types of medical device systems. For example, the elongated members described herein may be used with medical devices used to deliver neurostimulation therapy (e.g., spinal cord stimulation), deep brain stimulation, stimulation of one or more muscles, muscle groups or organs, and, in generally, stimulation of tissue of a patient. In other applications, the elongated members described herein can be used in medical systems that provide muscular stimulation therapy, gastric system stimulation, nerve stimulation, lower colon stimulation, recording or monitoring, gene therapy, or the like.

Additionally, in some embodiments the elongated members described herein can be catheters for dispensing a drug or other beneficial agent from an implanted or external drug delivery device. In short, the elongated members described herein can find useful applications in a wide variety of medical devices that implement elongated members for delivery of therapy to a patient. The patient may be a human patient. In some cases, however, the elongated members described herein may be applied to non-human patients.

An elongated member described herein includes features that allow the lead to extend. At least a portion of the elongated member is coiled or otherwise gathered within a sheath, and as tensile forces are applied to the elongated member in a direction substantially parallel to the longitudinal axis of the sheath, the coiled or otherwise gathered portion of the elongated member may uncoil or otherwise extend outside of the sheath. The sheath helps minimize tissue ingrowth around the coiled or gathered section of the elongated member, which would potentially limit the ability of the elongated member to uncoil and extend.

FIG. 1 is a conceptual diagram illustrating an exemplary implantable medical system 10 comprising IMD 12, and implantable medical leads 14, 16 electrically coupled to IMD 12. In the embodiment shown in FIG. 1, system 10 is implanted to deliver stimulation therapy to heart 5 of patient 18. Patient 18 ordinarily will be a human patient. In some cases, however, the disclosed features may be applied to non-human patients. In the embodiment shown in FIG. 1, IMD 12 is a pacemaker. Leads 14, 16 each include at least one electrode that are each positioned within (e.g., intravenously) or proximate to heart 5 (e.g., an epicedial lead) in order to deliver therapeutic electrical stimulation (e.g., pacing or defibrillation pulses or continuous time signals) from IMD 12 to heart 5. In some embodiments, at least one of leads 14, 16 may provide stimulation to heart 5 without contacting heart 5, e.g., a lead including a subcutaneous electrode.

In different embodiments, IMD 12 may comprise any of a wide variety of medical devices that are configured to couple to one or more medical elongated members and deliver therapy to patient 18 via the elongated members. As non-limiting examples, IMD 12 may be an implantable cardiac pacemaker that provides therapeutic stimulation to heart 5, an implantable cardioverter, an implantable defibrillator or an implantable cardiac pacemaker-cardioverter-defibrillator (PCD). IMD 12 may deliver pacing, cardioversion or defibrillation signals to patient 18 via electrodes disposed proximate to the distal ends of one or more leads 14, 16. Accordingly, in different embodiments, leads 14, 16 may electrically couple one or more electrodes to IMD 12, and leads 14, 16 may be positioned to deliver therapeutic electrical signals (e.g., pulses or continuous signals) to various cardiac locations.

As previously described, however, leads 14, 16 described herein are not limited for use with pacemakers, cardioverters or defibrillators. For example, in other embodiments, leads 14, 16 may be used with patient monitoring devices or devices that integrate monitoring and stimulation features. In those cases, leads 14, 16 may include different configurations, such as sensors disposed on distal ends of the respective lead for sensing patient conditions or other configurations of electrodes, depending on the type of target stimulation site or type of electrical stimulation therapy delivered by leads 14, 16.

Figure 2:
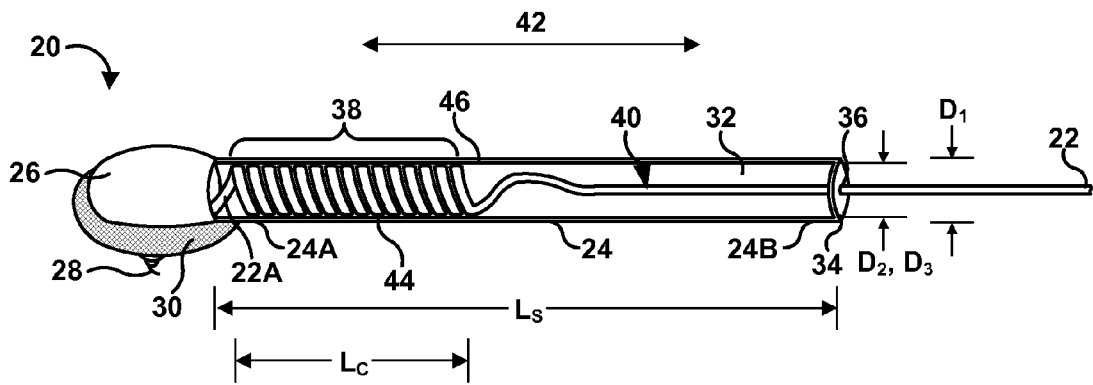
FIG. 2 is a side view diagram of an embodiment of an implantable medical lead that includes a sheath and a partially coiled lead body.

FIG. 2 is a side view of an embodiment of a lead 20, which may, for example, correspond to either of leads 14, 16 of FIG. 1. Lead 20 includes lead body 22, sheath 24, and electrode head 26. At least a portion of lead body 22 is coiled into a coiled section 38 that is enclosed by sheath 24. In FIG. 2, lead body 22 is in an unextended configuration. The proximal end (not shown) of lead 20 may be electrically and/or mechanically coupled to an implantable medical device, such as IMD 12, either directly or indirectly (e.g., via a lead extension). In the case of lead 20 that delivers electrical stimulation to patient 18, conductors disposed in lead body 22 electrically connects electrode 28 (and any other stimulation or sensing electrodes, if present) proximate lead body distal end 22A to a source of electrical stimulation housed by IMD 12.

Figure 4:
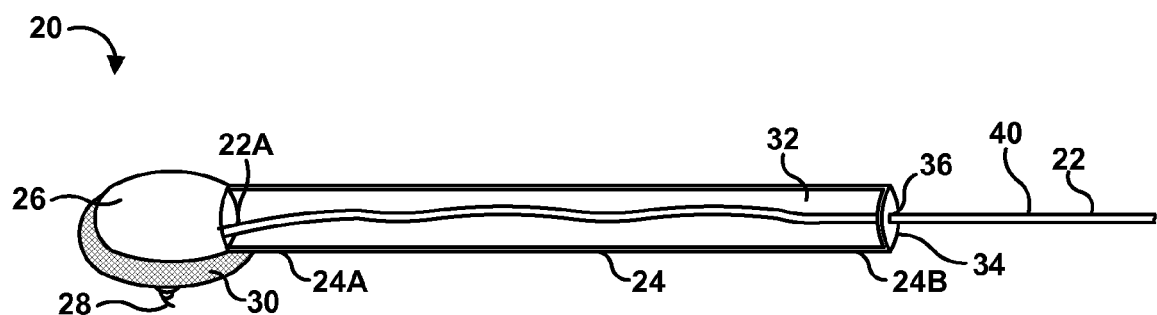
FIG. 4 is a side view diagram illustrating the lead of FIG. 2, where the partially coiled lead body has been extended.

At least a portion of lead body 22 disposed within sheath 24, and, in some embodiments, the entire lead body 22 is flexible in order to help coil lead into coiled section 38. In one embodiment, lead body 22 exhibits sufficient flexibility to be coiled into helical coils with an outer diameter of less than about 0.50 centimeters (cm), such as about 0.25 cm. Further, the materials used to form at least the portion of lead body 22 disposed within sheath 24 preferably do not have shape memory. That is, the materials used to form at least the portion of lead body 22 surrounded by sheath 24 do not attempt to recover their initial state during or after lead body 22 is pulled from an unextended configuration (FIG. 2) to an at least partially extended configuration (e.g., as shown in FIG. 4). Accordingly, lead body 22 does not exert any restorative forces on the proximal end (not shown in FIG. 2) or distal end 22A of lead body 22 when lead 20 is extended from an unextended configuration, as shown in FIG. 2, to an extended configuration, e.g., as shown in FIG. 4.

Lead body 22 may comprise any one or more insulated conductors, such as insulated ribbon wires, insulated solid conductors, insulated cable conductors or insulated braided stranded conductors. In some preferred embodiments, lead body 22 comprises a conductor coiled around a fiber core. Each conductor may be electrically coupled to one or more electrodes 28. In the embodiment shown in FIG. 2, lead body 22 includes a single conductor electrically coupled to electrode 28. In one embodiment, lead body 22 comprises one or more braided stranded conductors, which may enhance the flexibility of lead body 22. The insulation may include any suitable electrically insulating material including, for example, silicone, polyurethane, polytetrafluoroethylene, and the like.

In the embodiment illustrated in FIG. 2, lead 20 includes a single electrode 28 located at distal end 22A of lead body 22 and coupled to electrode head 26. An electrical conductor disposed within lead body 22 electrically couples to electrode 28 via electrode head 26. The electrical conductor may electrically couple electrode 28 to a source of electrical stimulation therapy within IMD 12. In other embodiments, lead 20 may include more than one electrode, and the electrodes may be coupled to lead body 22 at any desired location along lead 20. In some embodiments that include more than one electrode 28, lead body 22 may include multiple individually-insulated conductors, such as one conductor for each electrode 28. In other embodiments that include more than one electrode 28, a single conductor may couple two or more electrodes 28 to the implantable medical device, such as IMD 12.

Electrodes 28 may be formed from a variety of electrically conductive, biocompatible materials. Example electrode materials include platinum and platinum iridium. Electrode 28 may include ring electrodes, segmented ring electrodes spiral electrodes (as shown in FIG. 2), and the like. Electrode 28 defines a generally helical shape such that electrode 28 may be fixed at a stimulation site. Thus, in the illustrated embodiment, electrode 28 defines a fixation element, namely a spiral or helix that punctures and screws into tissue at or near a target stimulation site. In this way, electrode 28 may contact tissue at a target stimulation site, as well as substantially fix itself at the target stimulation site. However, additional fixation elements may also be used instead of or in addition to electrode 28. In some embodiments, a clinician may fix lead 22 at the stimulation site with the aid of an implantation tool that grips electrode head 26 at a distal end of the tool. The clinician may manipulate distal end 22A of lead body 22 from a proximal end of lead body 22 with the aid of the implantation tool in order to twist electrode 28 and advance electrode 28 into tissue.

In other embodiments, lead 20 may be fixed at a target therapy delivery site via any suitable technique. For example, a fixation mechanism may include self-actuating or physician-actuated tines, hydrogel elements, flanges, adhesives, and the like. The fixation mechanism may be separate from electrode 28, or may include electrode 28, as in FIG. 2. In some embodiments, the fixation mechanism comprises stainless steel or another biocompatible metal, a biocompatible plastic, or the like.

In some embodiments, including the illustrated embodiment, lead 20 also includes mesh 30 to aid fixation of lead 20 at a desired stimulation site. Mesh 30 facilitates tissue ingrowth, which further anchors electrode 28 proximate to the target stimulation site. Mesh 30 may comprise a woven cloth, a woven or molded polymer, or the like. In one embodiment mesh 30 includes a Dacron polyethylene terephthalate mesh.

Sheath 24 defines cavity 32 that encloses at least a length of lead body 22. In the embodiment shown in FIG. 2, the length of lead body 22 enclosed by sheath 24 includes coiled section 38 and substantially uncoiled section 40. In the illustrated embodiment, sheath distal end 24A is mechanically coupled to electrode head 26. In other embodiments, sheath distal end 24A of sheath 24 may be mechanically coupled to lead body 22 proximate the lead body distal end 22A.

Sheath 24 comprises a bio-compatible material that is substantially body tissue impermeable, such as a bio-compatible polymer. In some embodiments, sheath 24 is substantially flexible. For example, sheath 24 may be comprised of silicone, polyurethane or the like. In order to help minimize the invasiveness of a procedure for implanting lead 20 within patient 18, as well as any discomfort to patient 18 from implanted lead 20, it may be desirable to minimize overall size of the lead 20, which includes lead body 22 and sheath 24. Accordingly, it may be desirable to limit the size (e.g., overall outer diameter $D_1$) of sheath 24, which depends upon the size of lead body 22.

Sheath 24 may be configured to have a sufficient size to enable cavity 32 to contain at least a length of lead body 22, i.e., coiled section 38 and substantially uncoiled section 40 of lead body 22. Because lead body 22 has a discrete size, coiled section 38 of lead body 22 has a minimum size that is dependent on the diameter of lead body 22. That is, coiled section 38 of lead body 22 has a certain minimum diameter $D_2$. The diameter $D_2$ of the coiled section 38 is measured from the outer surface of one side of the coil (adjacent to an inner surface of sheath 24) to the outer surface of the other side of the coil (adjacent to an inner surface of sheath 24). In the embodiment shown in FIG. 2, the diameter $D_2$ of the coiled section 38 is substantially equal to or slightly greater than the inner diameter $D_3$ of the sheath 24 in its relaxed state. Thus, inner diameter $D_3$ of sheath 24 may have a respective minimum diameter that is sized to accommodate the diameter $D_2$ of coiled section 38 of lead body 22.

In addition, lead 20 may be constructed to minimize the thickness of sheath 24 walls (i.e., $(D_1-D_3)/2$) in order to help minimize the invasiveness of the implantation of lead 20 within patient 18. In one embodiment, a thickness of sheath 24 walls is less than about 0.5 millimeters (mm), such as about 0.381 mm (about 0.015 inches).

Coiled section 38 of lead body 22 is configured to at least partially uncoil and extend outside of sheath 24 upon the application of tensile force to lead body 22 (generally in the direction indicated by arrow 42 in FIG. 2). In the embodiment shown in FIG. 2, coiled section 38 of lead body 22 is configured to uncoil upon the application of tensile force at either distal end 22A of lead body 22 or the lead body proximal end in a direction substantially parallel to a major axis of sheath 24. Both the size (i.e., length $L_c$ and diameter $D_2$) of coiled section 38 and sheath 24 may be selected to accommodate the desired length of extension of lead body 22. For example, coiled section 38 of lead body 22 may be sized to enable lead body 22 to extend a relatively large amount, such as up to or more than about 10 cm. In other embodiments, coiled section 38 may be configured to enable lead body 22 to extend up to about 24 cm. In order to achieve the desired amount of lead body 22 extension, an "excess length" of lead body 22 that corresponds to the desired amount of lead body 22 extension may be enclosed by sheath 24. For example, if about 10 cm of lead body 22 extension is desired, an excess length of about 10 cm to about 13 cm of lead body 22 may be coiled to define coiled section 38. However, depending upon the size of lead body 22 and the length of the resulting coiled section 38, more excess length may be needed. Length $L_c$ of coiled section 38 may depend upon the number of turns (or "coils") of lead body 22. For example, if about 12 to about 15 turns (or "coils") of lead body 22 are disposed within sheath 24, the length $L_c$ of coiled section 38 may be about 12 to about 15 times the diameter $D_6$ (FIG. 3) of lead body 22.

Sheath 24 is configured to contain the excess length of lead body 22. That is, internal diameter $D_3$ and length $L_s$ of cavity 32 of sheath 24 may be selected to accommodate the excess lead body 22 length, i.e., the length of lead body 22 that is greater than the length $L_s$ of sheath 24. The excess lead body 22 length may be accommodated within sheath 24 by coiling at least a section of lead body 22 in a helical fashion with a major axis of the helix generally extending parallel to or coincident with a major axis of sheath 24 (as illustrated in FIG. 2). Alternatively, the excess lead body 22 length may be accommodated by coiling at least a section of lead body 22 in a generally axial direction of sheath 24, or by gathering at least a section of lead body 22 in an irregular pattern within sheath 24. In general, lead body 22 may be arranged within cavity 32 such that lead body 22 does not tangle as it is pulled from sheath 24. Tangling may prevent the withdrawal of lead body 22 from sheath 24 via a force that is less than the force required to dislodge electrode 28 from the target stimulation site. It is desirable for lead body 22 to be pulled from sheath 24 with a force that does not result in the dislodging of electrode 28 from a target stimulation site.

While coiled section 38 of lead body 22 may occupy the entire length $L_s$ of sheath 24, in some embodiments, such as the embodiment illustrated in FIG. 2, it may be desirable to limit the length $L_c$ of coiled section 38 to less than about half of length $L_s$ of sheath 24 in order to provide room for lead body 22 to at least partially uncoil prior to exiting sheath 24. If lead body 22 uncoils at aperture 36 of sheath 24, the tensile force necessary to pull a length of lead body 22 from sheath may increase due to the additional force necessary to pull a coil through aperture 36.

In addition to selecting the length $L_s$ of the sheath 24 to accommodate the desired excess length of lead body 22, inner diameter $D_3$ of sheath 34 may be sized to accommodate the desired outer diameter $D_2$ of the coiled section 38 of lead body 22. In some embodiments, inner diameter $D_3$ of sheath 24 is selected such that the outer surface 44 of coiled section 38 of lead body 22 contacts the inner wall 46 of the sheath 24, i.e., there is an interference fit between coiled section 38 of lead body 22 and inner wall of sheath 24. The friction due to this contact may help keep coil section 38 organized, thereby minimizing or even eliminating tangles that would partially or fully prevent lead body 22 from being pulled out of sheath 24. In some embodiments it may be preferred to form the coil section 38 in coils as small as the flexibility of lead body 22 will allow, and to size the inner diameter $D_3$ of the sheath substantially the same as the resulting diameter $D_2$ of coiled section 38.

While the sheath 24 may comprise a wide range of lengths and diameter, particularly in embodiments in which lead 20 carries an epicardial electrode 28, in some embodiments outer diameter $D_1$ of sheath 24 is sized such that transvenous implantation is feasible. For example, in some embodiments, outer diameter $D_1$ of sheath 24 is less than about 14 French (about 0.467 cm), and such as about 11 French (about 0.366 cm). In embodiments using a sufficiently flexible lead body 22, outer diameter $D_1$ of sheath 24 may be about 9 French (about 0.300 cm) or less.

Figure 3:
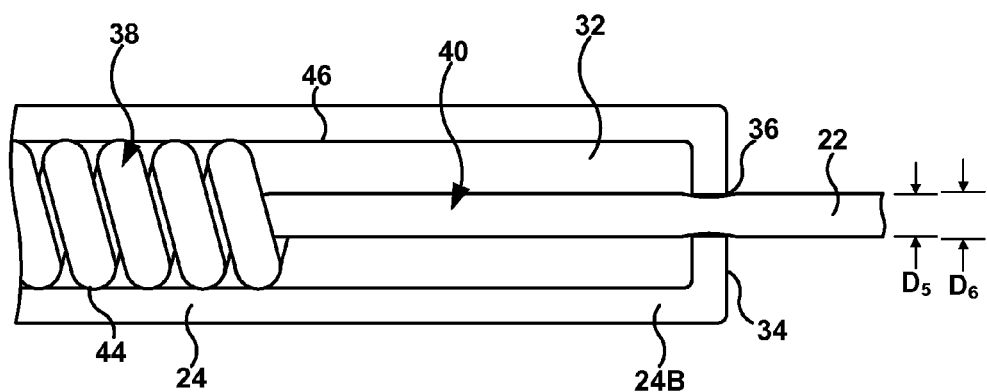
FIG. 3 is a cross-sectional view of the lead of FIGS. 2 and 3, and illustrates a sheath including a seal.

As shown in further detail in FIG. 3, proximal end 24B of sheath 24 form a seal 34 that defines an aperture 36 through which lead body 22 extends. In other embodiments, seal 34 may be separate from and coupled to sheath 24. Further, in some embodiments, sheath may not include a seal 34. Seal 34 may generally comprise any suitable biocompatible material, such as a biocompatible polymer. In some preferred embodiments, seal 34 may comprise silicone, polyurethane, or the like.

Seal 34 defines an aperture 36 that does not substantially impede lead body 22 from exiting sheath 24 when a tensile force is applied to lead body 22 in a direction indicated by arrow 42 in FIG. 2, e.g., a tensile force from either a distal end 22A, proximal end (not shown) of lead body 22 or anywhere along lead body 22. Specifically, a length of lead body 22 that is contained within cavity 32 may exit cavity 32 via aperture 36 in response to an applied tensile force. The tensile force may be due to a number of factors, such as a patient's movement, a patient's growth, a patient's heart beat, purposeful application of a tensile force by a clinician or the like.

In the embodiment shown in FIG. 3, seal 34 forms an intimate fit with lead body 22, such that seal 34 defines a substantially fluid-impervious seal between sheath 24 and lead body 22. In this way, seal 34 substantially blocks contaminants, such as proteins, fluids, enzymes, and the like, from entering cavity 32. These contaminants may promote tissue ingrowth within cavity 32 and around coiled section 38 of lead body 22, which may prevent coiled section 38 from uncoiling and extending in response to a tensile force or increase the tensile force with which lead body 22 may be extended from cavity 32, i.e., the force required to at least partially uncoil coiled section 38. Thus, providing seal 34 between sheath 24 and lead body 22 may enable prolonged function of extendable lead 20 by preventing tissue ingrowth around the coiled section 38 of lead body 22.

In some embodiments, seal 34 is defined by sheath 24. For example, sheath 24 may define aperture 36 that is sized to substantially engage outer surface of lead 22. For example, in one embodiment, diameter $D_5$ of aperture 36 is less than or equal to diameter $D_6$ of lead body 22. In these embodiments, the diameter of aperture 36 relative to the diameter of lead body 22 is selected provide an intimate fit in order to substantially block the entry of contaminants into cavity 32, as described, as well as to provide a suitable amount of resistance to applied tensile forces. A suitable amount of resistance between seal 34 and lead body 22 may compensate for incidental movement of patient 18 (e.g., changes in posture) for which extension of lead 20 is not desired.

On the other hand, the interface between seal 34 and lead body 22 is also designed to allow lead body 22 to be pulled from sheath 24 prior to failure of a fixation mechanism such as spiral electrode 28 (e.g., before electrode 28 disengages from the tissue it is coupled to), before failure of any fixation mechanism used to attach proximal end of lead body 22 to an IMD, and before failure of any fixation mechanism used to anchor the implanted medical device in the desired location. In some embodiments, the interface between seal 34 and lead body 22 exerts a frictional force such that a tensile force of about 0.12 kg to about 2 kg is required to pull approximately 2.54 cm of lead body 22 from sheath 24. For example, in some embodiments, a tensile force of about 0.12 kg to about 0.28 kg is necessary to pull approximately 2.54 cm of lead body 22 from the sheath 24. In other embodiments, a tensile force of about 0.04 kg is necessary to pull approximately 2.54 cm of lead body 22 from the sheath 24.

To accomplish this range of tensile and frictional forces, diameter $D_5$ of aperture 36 is about 2% to about 60% smaller than outer diameter $D_6$ of lead body 22, such as about 5% to about 30% smaller than the diameter of lead body 22. In one embodiment, outer diameter $D_6$ of lead body 22 is about 0.086 cm and diameter $D_5$ of aperture 36 defined by silicone seal 34 is about 0.076 cm. Thus, in this embodiment, the diameter of the aperture 36 is about 12% smaller than the diameter of the lead body 22. This relative sizing requires a force of about 0.12 kg to about 0.28 kg to pull about 2.54 cm of lead body 22 from sheath 24.

As described briefly above, lead 20 preferably does not exert any restorative force on lead distal end 22A or the lead proximal end in an unextended, partially extended, or substantially fully extended state (up to the limit of a fully extended lead body 22). More specifically, once a tensile force is exerted on lead 20, a length of coiled section 38 of lead body 22 is uncoiled, and a length of substantially uncoiled section 40 is pulled from the sheath 24 and remains substantially pulled from sheath 24. In this way, lead body 22 does not exert any spring force or restorative force in an attempt to recover to the original, more fully coiled configuration. This may be accomplished through the selection of appropriate lead body 22 materials, including, for example, the particular conductor and electrically insulating material surrounding the conductors, as well as the configuration of the conductors and insulating material. Additionally, the intimate fit of seal 34 and lead body 22 may be designed such that the friction between seal 34 and lead body 22 resists an amount of restorative force up to the force required to initiate a pull of lead body 22 from sheath 24.

Preventing the exertion of any restorative force on distal end 22A and the proximal end of lead body 22 may help to minimize the stress on the electrode 28 interface, and also on any fixation mechanism at the proximal end of lead body 22 (e.g., the connection between the proximal end of lead body 22 and an IMD, or the fixation mechanism used to anchor the IMD to its implantation site). This may increase the reliability of lead 20 by decreasing the failure rate of a fixation mechanism, such as electrode 28, and subsequent migration of the electrode, the IMD, lead fracture, or disconnection of lead 20 from the IMD.

Mechanically coupling distal end 24A of sheath 24 proximate to lead body distal end 22A may provide flexibility. For example, the movement of lead body 22 may become restricted at intermediate portion 8 (FIG. 1) between sheath proximal end 24B and the proximal end of lead body 22, e.g., by tissue ingrowth around lead body 22. When this occurs, patient movement or growth may exert a tensile force between restricted portion 8 (FIG. 1) and electrode 28 or the target stimulation site. If lead body 22 is not permitted to extend between intermediate portion 8 and electrode 28, electrode 28 may become detached from the target stimulation site, thereby compromising the effectiveness of the therapy system. That is, extension of lead body 22 between intermediate portion 8 and IMD 12 may be insufficient to reduce stresses at electrode 28. In order to help reduce stress at electrode 28, it may be desirable to provide an extension mechanism, such as coiled section 38/sheath 24, proximate the electrode 28 or the target stimulation site, or as in the illustrated embodiment, near electrode head 26. Accordingly, a lead 20 that permits lead body 22 to extend near electrode head 26 may help reduce stresses on electrode 28 at the target stimulation site, where the stresses are attributable to patient growth or movement.

FIG. 4 is a side view diagram illustrating the lead 20 of FIG. 2 in a substantially fully extended configuration. As tensile forces (due to growth, movement, or the like) are exerted on lead body 22, excess length of lead body 22 contained within sheath 24 is dispensed from sheath 24. In this way, lead body 22 has the capacity to extend its length. FIG. 4 shows a state in which lead body 22 has been fully extended, i.e., a state in which coiled section 38 of lead body 22 has uncoiled and any excess length of lead body 22 has been pulled from sheath 24. As briefly discussed above, sheath 24 is configured such that lead body 22 substantially uncoils prior to or as lead body 22 extends through sheath 24. This prevents, among other things, any bends in lead body 22 due to coiling from increasing the force required to pull a length of lead body 22 from sheath 24.

As one example, extension of lead 20 may be desirable if patient 18 is a pediatric patient. As patient 18 grows, the distance between heart 5 and the implant site for IMD 12 (e.g., in a subcutaneous pocket in the patient's chest) may increase, thereby applying tensile forces to lead body 22, and increasing the risk of decoupling electrode 28 from the target stimulation site. Lead 20 is configured to extend to accommodate the increased distance between heart 5 and IMD 12 and help reduce any forces that may potentially decouple electrode 28 from the target stimulation site.

Figure 5:
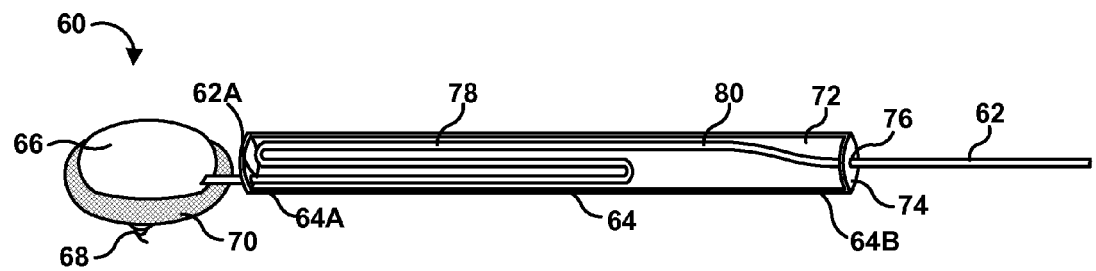
FIG. 5 is a side view diagram of another embodiment of an implantable medical lead that includes a sheath and a gathered lead.

FIG. 5 is a side view diagram of another embodiment of extendable lead 60, which includes lead body 62 and sheath 64. In this illustrated embodiment, a distal end 64A of sheath 64 is mechanically coupled to lead body 62 proximate to lead body distal end 62A. The mechanical coupling fixes the sheath 64 relative to lead body 62 at the sheath distal end 64A. Sheath 64 may couple to lead body 62 via any suitable coupling mechanism, such as friction, an adhesive, or a mechanical attachment mechanism, such as a loop or hook.

In contrast to the embodiment shown in FIG. 2, lead body 62 is gathered substantially axially with respect to sheath 64 instead of being helically coiled. Similar to the embodiment shown in FIG. 2, lead body 62 may be pulled from sheath proximal end 64B through aperture 76 by an applied tensile force that results from patient movement, growth, or the like. Numbered elements 66, 68, 70, 72, 74, 78 and 80 correspond to elements 26, 28, 30, 32, 34, 38 and 40, respectively, illustrated in FIG. 2.

Figure 6:
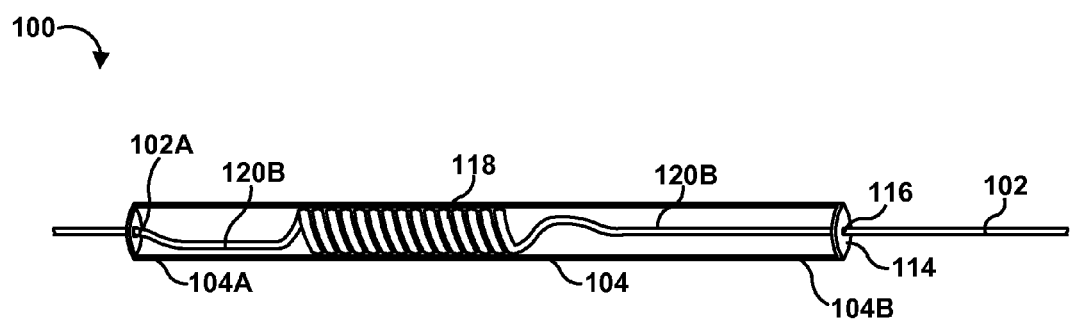
FIG. 6 is a side view diagram illustrating an embodiment of an implantable medical lead that includes a sheath located between the proximal and distal ends of the lead body.

FIG. 6 is a schematic side view of another embodiment of an extendable lead 100, which includes lead body 102 and sheath 104. Sheath 104 encloses a length of lead 102 via coiled section 118, as well as two substantially uncoiled sections 120A, 120B of lead body 102 substantially distal and proximate to coiled section 118. In this embodiment, sheath 104 is coupled to lead body 102 at an intermediate distance along the length of lead body 102. Sheath 104 may be coupled to lead body 102 at sheath distal end 104A, sheath proximal end 104B, or a section of sheath 104 adjacent to coiled section 118 of lead body 102. Coupling sheath 104 to lead body 102 at a section of sheath 104 adjacent coiled section 118 of lead body 102 may allow lengths of lead body 102 to be pulled from either, or both, sheath proximal end 104B and sheath distal end 104A. Sheath 104 may couple to lead body 102 via any suitable mechanism, such as friction, an adhesive, a mechanical attachment (e.g., a loop or hook). In some case, sheath 104 may be coupled to lead body 102 by a friction fit between coiled section 118 and an inner surface of sheath 104. Further, sheath 104 may include a fixation mechanism such as surgical adhesive, tines, flanges, sutures, hydrogel elements, and the like to anchor sheath 104 in a desired position within a body of patient 18. Elements 102A, 114 and 116 correspond to elements 22A, 34 and 36 respectively, illustrated in FIG. 2.

Figure 7:
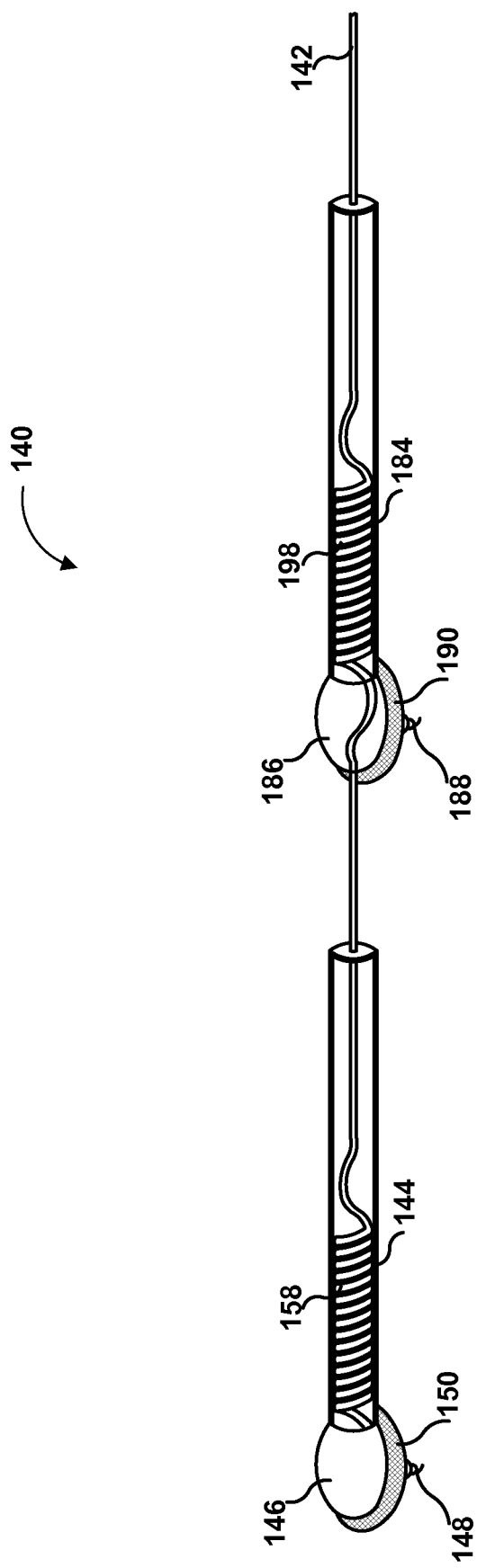
FIG. 7 is a side view diagram illustrating an embodiment of an implantable medical lead that includes two electrodes and two sheaths.

In other embodiments, such as that shown in FIG. 7, a lead 140 may include multiple electrodes 148, 188 and/or multiple sheaths 144, 184. Embodiments such as these may provide greater flexibility in maintaining a position of two electrodes 148, 188 despite patient growth or movement. For example, electrode 148 may be anchored in one position in a body of a patient using a fixation mechanism (e.g., the spiral shape of electrode 148) and tissue ingrowth aided by mesh 150. Similarly, electrode 188 may be anchored at a second position in a body of a patient using a fixation mechanism (e.g., spiral electrode 188) and tissue ingrowth aided by mesh 190. The first and second position may be any desired distance apart. Both electrodes 148, 188 may be electrically and mechanically coupled to an IMD via lead body 142. The section of lead body 142 between electrode housing 146 and electrode housing 186 is configured to extend in response to relative motion between electrodes 148, 188, whether this motion is due to growth or movement of the patient. In this way, electrodes 148, 188 may remain in place despite patient growth that increases a distance between the respective stimulation sites of electrodes 148, 188. Similarly, it may also be desirable for the section of lead body 142 that joins electrode 188 to the IMD to extend. Providing a sheath 144 and coiled lead body section 158 between electrodes 148 and 188 and another sheath 184 and coiled lead body section 198 between electrode 188 and the proximal end of lead body 142 (coupled to the IMD) may provide a lead 140 configured to accommodate growth of patient 18 when two or more electrodes are implanted within patient 18.

Sheath 144 and sheath 184 need not be the same length or diameter. Each sheath 144, 184 may be constructed according to the desired amount extension desired for lead body 142. Correspondingly, the length each coiled lead body section 158, 198 may be chosen to provide the desired amount of extension desired for each section of lead body 142.

An extendable elongated member including a sheath enclosing a length of an elongated member may be useful for various electrical stimulation systems. For example, the extendable elongated member may be used to deliver electrical stimulation therapy to patients to treat a variety of symptoms or conditions such as cardiac rhythm management. For example the elongated member may be an endocardial, epicardial or myocardial lead. As other examples, the elongated members may be useful for delivering electrical stimulation therapy to patients to treat chronic pain, tremor, Parkinson's disease, multiple sclerosis, spinal cord injury, cerebral palsy, amyotrophic lateral sclerosis, dystonia, torticollis, epilepsy, pelvic floor disorders, gastroparesis, muscle stimulation (e.g., functional electrical stimulation (FES) of muscles) or obesity. In addition, the sheath described herein may also be useful for enclosing a length of a catheter, such as a drug delivery catheter, to permit the catheter to extend its length.

Figure 8A:
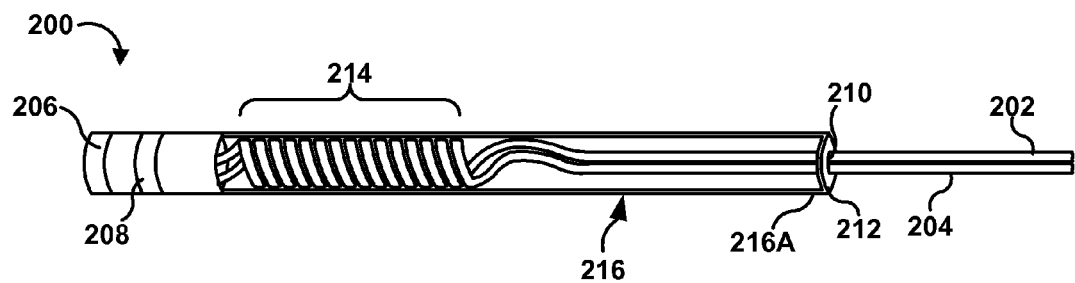
FIGS. 8A and 8B each illustrate an example lead assembly that includes multiple elongated members disposed in a common sheath.

In addition, a therapy system may include multiple extendable elongated members, such as bipolar lead including two lead bodies or a combination stimulation lead and fluid delivery catheter. In such embodiments, the multiple extendable elongated members may be disposed within respective sheath or within a common sheath. For example, FIG. 8A shows a bipolar lead assembly 200 including two leads bodies 202, 204 with respective electrodes 206, 208. The lead bodies 202, 204 are coiled together within sheath 216 in coiled section 214, and exit sheath distal end 216A of sheath 216 through a common aperture 210 in seal 212. Seal 212 may be similar to seal 34 described above. However, aperture 210 may be sized to accommodate multiple lead bodies 202, 204.

Figure 8B:
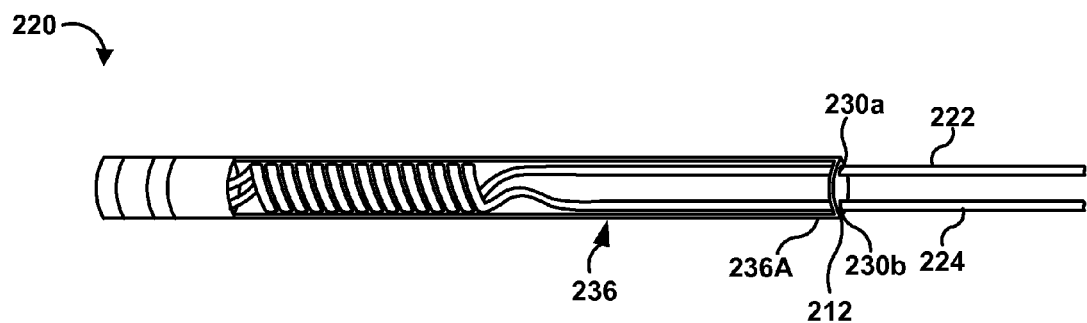

FIG. 8B shows another exemplary embodiment of a bipolar lead assembly 220. In this embodiment, lead bodies 222, 224 are again disposed within a common cavity of a common sheath 236 and coiled together. However, in contrast to the embodiment shown in FIG. 8A, seal 212 coupled to sheath proximal end 236a defines two apertures 230a, 230b through which lead body 222 and lead body 224 exit, respectively.

Figure 8C:
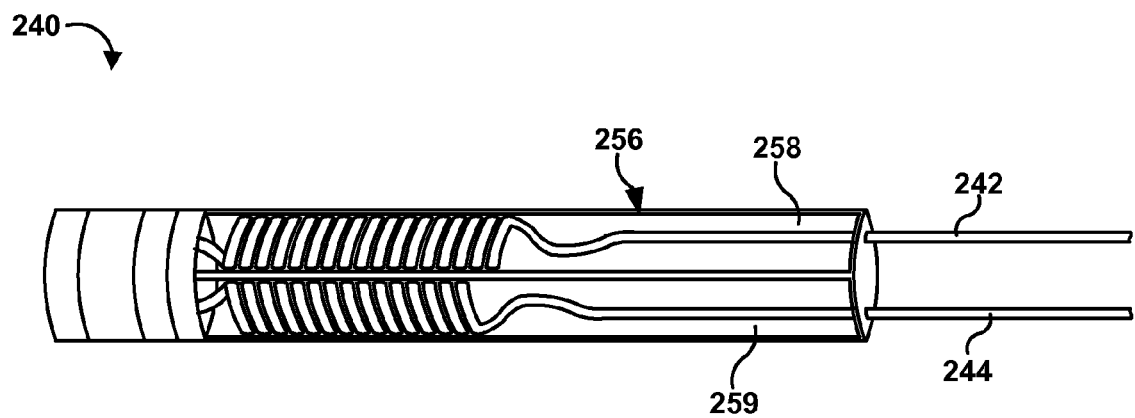
FIG. 8C illustrates an example lead assembly that includes a sheath that defines separate cavities for respective elongated members.

While FIGS. 8A and 8B illustrate elongated member assemblies that include multiple leads in a common cavity of a sheath, in other embodiments, an assembly may include multiple elongated members (e.g., leads or catheters) within separate sheaths or separate cavities of a common sheath. FIG. 8C is a schematic illustration of lead assembly 240 that includes sheath 256 that defines separate cavities 258, 259 (e.g., adjacent cavities) for respective elongated member 242, 244. In other embodiments, separate elongated members may be housed within separate sheaths that are not coupled together. Furthermore, elongated member assemblies may include more than two elongated members. In general, a combination of separate sheaths and common sheaths may be used for therapy systems including more than two extendable elongated members.

Various embodiments of the invention have been described. These and other embodiments are within the scope of the following claims.

The invention claimed is:
1. An assembly comprising:
an implantable medical elongated member having a proximal end and a distal end;
a sheath defining a cavity and comprising a sheath proximal end and a sheath distal end, wherein a length of the elongated member is enclosed within the cavity; and
a seal coupled to at least one of the sheath distal end or the sheath proximal end, the seal defining an aperture through which the elongated member extends, wherein the seal substantially prevents contaminant entry into the cavity of the sheath, and
wherein a portion of the length of the elongated member enclosed within the sheath exits the cavity through the aperture defined by the seal when a tensile force is applied to the elongated member; and wherein the elongated member does not exert a restorative force after the portion of the length of the elongated member exits the cavity.

2. The assembly of claim 1, wherein the seal and sheath are substantially integral.

3. The assembly of claim 1, wherein a first diameter of the aperture is substantially equal to or less than a second diameter of the elongated member.

4. The assembly of claim 1, wherein at least a section of the length of the elongated member within the cavity is helically wound.

5. The assembly of claim 4, wherein the helically wound section of the elongated member is friction fit with the sheath within the cavity.

6. The assembly of claim 1, wherein at least a section of the length of the elongated member within the cavity is substantially non-coiled.

7. The assembly of claim 1, wherein the sheath comprises silicone.

8. The assembly of claim 1, wherein the length of the elongated member is enclosed within the sheath such that a tensile force of about 0.12 kilograms (kg) to about 2 kg applied to at least one of the distal or proximal ends of the elongated member withdraws about 2.54 cm of the elongated member from the sheath.

9. The assembly of claim 1, wherein a diameter of the sheath is less than about 14 French.

10. The assembly of claim 1, wherein the portion of the elongated member is at least about 7 centimeters long.

11. The assembly of claim 1, further comprising an implantable medical device coupled to the elongated member.

12. The assembly of claim 1, wherein the sheath comprises a first sheath, the cavity comprises a first cavity, and the length of the elongated member comprises a first length, the medical assembly further comprising a second sheath defining a second cavity and a sheath length, wherein a second length of the elongated member is enclosed within the cavity, the second length being greater than the sheath length.

13. The assembly of claim 12, further comprising an electrode coupled to the elongated member between the first and second sheaths.

14. The assembly of claim 1, wherein the implantable medical elongated member comprises a first implantable medical elongated member, the length enclosed within the cavity comprises a first length, and the portion that exits the cavity through the aperture comprises a first portion, wherein the assembly further comprises a second implantable medical elongated member, wherein a second length of the second elongated member is enclosed within the cavity, and wherein a second portion of the length of the second elongated member enclosed within the sheath exits the cavity through the aperture defined by the seal when a tensile force is applied to the second elongated member.

15. The assembly of claim 1, wherein the implantable medical elongated member comprises a first implantable medical elongated member, the length enclosed within the cavity comprises a first length, the aperture comprises a first aperture, and the portion that exits the cavity through the first aperture comprises a first portion, wherein the assembly further comprises a second implantable medical elongated member, wherein a second length of the second elongated member is enclosed within the cavity, wherein the seal defines a second aperture through which the second implantable medical elongated member extends and wherein a second portion of the length of the second elongated member enclosed within the sheath exits the cavity through the second aperture when a tensile force is applied to the second elongated member.

16. The assembly of claim 1, wherein the elongated member comprises at least one of a medical lead comprising an electrode or a catheter comprising a fluid delivery conduit.

17. An assembly comprising:
an implantable medical elongated member having a proximal end and a distal end;
a sheath defining a cavity and comprising a sheath proximal end and a sheath distal end, wherein a length of the elongated member is enclosed within the cavity; and
a seal coupled to at least one of the sheath distal end or the sheath proximal end, the seal defining an aperture through which the elongated member extends, wherein the seal substantially prevents contaminant entry into the cavity of the sheath, and
wherein a portion of the length of the elongated member enclosed within the sheath exits the cavity through the aperture defined by the seal when a tensile force is applied to the elongated member; and
wherein the elongated member does not exert a force tending restore the portion of the elongated member to a form it had before exiting the cavity, after the portion of the length of the elongated member exits the cavity.

18. The assembly of claim 17, wherein the seal and sheath are substantially integral.

19. The assembly of claim 17, wherein a first diameter of the aperture is substantially equal to or less than a second diameter of the elongated member.

20. The assembly of claim 17, wherein at least a section of the length of the elongated member within the cavity is helically wound.

21. The assembly of claim 20, wherein the helically wound section of the elongated member is friction fit with the sheath within the cavity.

22. The assembly of claim 17, wherein at least a section of the length of the elongated member within the cavity is substantially non-coiled.

23. The assembly of claim 17, wherein the sheath comprises silicone.

24. The assembly of claim 17, wherein the length of the elongated member is enclosed within the sheath such that a tensile force of about 0.12 kilograms (kg) to about 2 kg applied to at least one of the distal or proximal ends of the elongated member withdraws about 2.54 cm of the elongated member from the sheath.

25. The assembly of claim 17, wherein a diameter of the sheath is less than about 14 French.

26. The assembly of claim 17, wherein the portion of the elongated member is at least about 7 centimeters long.

27. The assembly of claim 17, further comprising an implantable medical device coupled to the elongated member.

* * * * *